United States Patent [19]
Pillay et al.

[11] Patent Number: 6,090,411
[45] Date of Patent: Jul. 18, 2000

[54] MONOLITHIC TABLET FOR CONTROLLED DRUG RELEASE

[75] Inventors: Viness Pillay, Philadelphia; Reza Fassihi, Ambler, both of Pa.

[73] Assignee: Temple University, Philadelphia, Pa.

[21] Appl. No.: 09/037,096

[22] Filed: Mar. 9, 1998

[51] Int. Cl.$^7$ .............................. A61K 47/02; A61K 9/22; A61K 47/38; A61K 47/34
[52] U.S. Cl. ....................... 424/468; 424/486; 424/488; 514/960
[58] Field of Search .................................... 424/486, 488, 424/466, 465, 468; 514/960

[56] References Cited

U.S. PATENT DOCUMENTS

| | | |
|---|---|---|
| 3,917,813 | 11/1975 | Pedersen . |
| 3,954,959 | 5/1976 | Pedersen . |
| 4,755,180 | 7/1988 | Ayer et al. . |
| 4,777,033 | 10/1988 | Ikura et al. . |
| 4,898,737 | 2/1990 | Panoz et al. . |
| 4,919,938 | 4/1990 | Lovegrove et al. . |
| 4,946,686 | 8/1990 | McClelland et al. . |
| 4,966,768 | 10/1990 | Michelucci et al. . |
| 5,002,776 | 3/1991 | Geoghegan et al. . |
| 5,518,737 | 5/1996 | Urtti et al. . |
| 5,520,931 | 5/1996 | Persson et al. . |
| 5,529,790 | 6/1996 | Eichel et al. . |
| 5,529,791 | 6/1996 | Deboeck et al. . |
| 5,560,928 | 10/1996 | DeFelice . |
| 5,603,955 | 2/1997 | Gehrke et al. . |

OTHER PUBLICATIONS

Perez–Marcos et al.; "Influence of pH on the Release of Propranolol Hydrochloride from Matrices Containing Hydroxypropylmethylcelluslose K4M and Carbopol 974", *J. Pharm. Sci.*, v. 85, Mar. 1996, 330–4.

Chakrabarti et al; "Control of Poorly Soluble Drug Dissolution in Conditions Simulating the Gastrointestinal Tract Flow. 1. Effect of Tablet Geometry in Buffered Medium"; *J. of Pharm. Sci.*, v. 85, Mar. 1996, pp. 313–319.

Chakrabarti et al.; "Control of Poorly Soluble Drug Dossolution in Conditions Simulating the Gastrointestinal Tract Flow. 2. Cocompression of Drugs with Buffers"; *J. of Pharm. Sci.*, v. 86, 1997, pp. 465–469.

Mooney et al.; "Dissolution Kinetics of Carboxylic Acids I: Effect of pH under Unbuffered Conditions"; *J. of Pharm. Sci.*, v. 70, Jan. 1981, pp. 13–22.

Mooney et al., "Dissolution Kinetics of Carboxylic Acids II: Effect of Buffers"; *J. of Pharm. Sci.*, v. 70, Jan. 1981, pp. 22–32.

Aunins et al., "Dissolution of Carboxylic Acids III: The Effect of Polyionizable Buffers"; *J. of Pharm. Sci.*, v. 74; Dec. 1987, pp. 1305–1316.

Neervannan et al., "A Convective–Diffusion Model for Dissolution of Two Non–interacting Drug Mixtures from Co–compressed Slabs Under Laminar Hydrodynamic Conditions"; *Pharm. Research*, v. 11, 1994, pp. 1288–1295.

Southard et al., "Dissolution of Ionizable Drugs into Unbuffered Solution: A Comprehensive Model for Mass Transport and Reaction in the Rotating Disk Geometry"; *Pharm. Research*, v. 9, 1992, pp. 58–69.

McNamara et al., "Dissolution of Acidic and Basic Compounds from the Rotating Disk: Influence of Convective Diffusion and Reaction"; *J. of Phrm. Sci.*, v. 75, Sep. 1986, pp. 858–868.

*Primary Examiner*—Edward J. Webman
*Attorney, Agent, or Firm*—Ratner & Prestia

[57] ABSTRACT

A swellable hydrophillic matrix tablet that delivers drugs in a controlled manner over a long period of time and is easy to manufacture. More specifically, the drug is disposed in a matrix composed of HPMC or polyethylene oxide, in the presence of a salt, which may be a combination of salts. Suitable salts include sodium bicarbonate, sodium chloride, potassium bicarbonate, calcium chloride, sodium bisulfate, sodium sulfite, and magnesium sulfate. Outward diffusion of the drug is controlled by an inwardly progressing hardening reaction between the salt and the dissolution medium, possibly also involving the drug itself.

7 Claims, 17 Drawing Sheets

MONOLITHIC TABLET FOR CONTROLLED DRUG RELEASE

BACKGROUND OF THE INVENTION

The present invention pertains to a controlled release dosage form, based on a modified hydrophillic matrix composition.

Controlled release pharmaceutical dosage forms have received much attention in recent years and are highly desirable for providing a constant level of pharmaceutical agent to a patient over some extended period of time. The use of single or multiple unit dosage forms as controlled drug delivery devices encompasses a wide range of technologies and includes polymeric as well as nonpolymeric excipients. These dosage forms optimize the drug input rate into the systemic circulation, improve patient compliance, minimize side effects, and maximize drug product efficacy.

The use of controlled release products is frequently necessary for chronic drug administration, such as in the delivery of the calcium-channel blockers nifedipine and diltiazem and the beta-adrenergic blocker Propranolol in the management of angina and hypertension For delivery system design, physiochemical properties and intrinsic characteristics of the drug, such as high or low solubility, limited adsorption, or presystemic metabolism, may impose specific constraints during product development.

Advancements of extended release drug products have come about by the simultaneous convergence of many factors, including the discovery of novel polymers, formulation optimization, better understanding of physiological and pathological constraints, prohibitive cost of developing new drug entities, and the introduction of biopharmaceutics in drug product design.

One aspect of research about controlled-release delivery systems involves designing a system which produces steady-state plasma drug levels, which is also referred to as zero-order drug release kinetics. To meet this objective, numerous design variations have been attempted, and their major controlling mechanisms include diffusion/dissolution, chemical reactions, the use of osmotic pump devices, and multiple layer tablet designs, all of which incorporate numerous manufacturing steps and many associated drug release mechanisms. The complicated processes involved in the manufacture of such ultimately contributes to increased costs to the consumer.

One attractive design for potential zero-order drug release is the use of hydrophilic swellable matrices. Drug diffusion from the matrix is accomplished by swelling, dissolution and/or erosion. The major component of these systems is a hydrophilic polymer. In general, diffusivity is high in polymers containing flexible chains and low in crystalline polymers. With changes in morphological characteristics, the mobility of the polymer segments will change and diffusivity can be controlled. Addition of other components, such as a drug, another polymer, soluble or insoluble fillers, or solvent, can alter the intermolecular forces, free volume, glass transition temperature, and consequently, can alter the transport mechanisms. Cost is also a factor in these modified compositions. Still better controlled, time dependent drug release from these compositions is a continuing objective of research in this area, as is controlled diffusivity compositions which are more easily manufactured. Such compositions, which are more easily manufacturable, have the potential to lower cost of the dosage form.

SUMMARY OF THE INVENTION

The present invention is a new monolithic dosage form that delivers pharmaceutically active agents in a controlled release manner, and that is easy to manufacture. This dosage form, in a form such as a monolithic tablet, may approach zero order delivery of drugs which are either of high or low solubility. This dosage form or tablet is comprised of a hydrophilic swellable matrix, in which is disposed a pharmaceutically active agent and a salt The salt, either in combination with the drug or another salt upon reaction in an aqueous medium, causes a hardening reaction of the matrix. The rate of outward diffusion is controlled by exposing the product to an aqueous medium. This in turn causes a hardening reaction to occur in a time dependent manner from the outer boundaries towards the inner boundaries of the product; the hardened reaction product, in turn limits outward diffusion of the drug as the inward ingress of aqueous medium causes a progressive hardening from the outer boundaries of the dosage form or tablet in a direction towards the inner core there.

DETAILED DESCRIPTION OF THE INVENTION

The invention encompasses formulations for the controlled release, preferably zero order release, of bioactive material from a new monolithic system.

These formulations are based on simple swellable hydrodynamically balanced monolithic matrix tablet in which may be incorporated a range of water-soluble (low to high) bioactive drugs and salts. Extended or zero order release is accomplished through the novel application of polymeric matrix modification, as detailed below, by incorporating a salt in a swellable matrix:

As a tablet passes through the human digestive tract, it is subjected to pH values ranging from 1.5 to 7.4. The saliva of the mouth has a neutral pH, the stomach has a pH varying from 2.0–4.0, and the pH of the intestines carries a pH between 5.0–7.5. Therefore, it is important to consider the effects of this pH range on dissolution of a drug tablet. For a drug to approach zero-order release, it's dissolution must be independent of the pH in the surrounding environment.

Through processes of ionic interaction/complexation/ molecular and/or self association between a drug and a salt or salt/drug combinations, homogeneously dispersed in a swellable polymer such as hydroxypropylmethylcellulose (HPMC), modify the dynamics of the matrix swelling rate and erosion of the swellable polymer, in accordance with variations in an external pH environment ranging from 1.5–7.0.

These interactions result in controlled matrix hardening. Such hardening is responsible for the control of polymer erosion/dissolution and drug release rates. By design, solvent penetrates the periphery of the tablet and a rapid initial interaction between drug and salt embedded in the polymeric matrix causes immediate hardening of the outer tablet boundary, the rate of hardening consistently decreases toward the center of the matrix core in a time-dependent manner over a long period of time (e.g. 24 hours).

Figure 18:
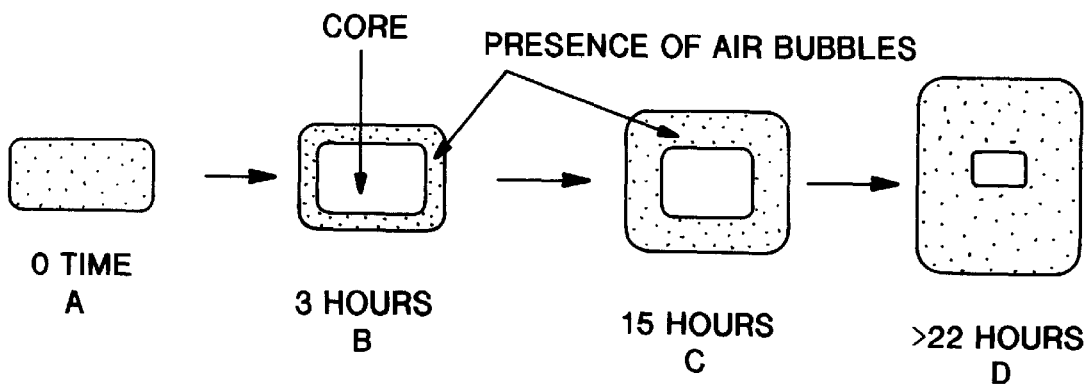
FIG. 18 is a schematic representation depicting the dissolution of the floatable monolithic matrix tablet over time.

The effervescent nature of sodium bicarbonate causes a generation of gas within the tablet and production of air bubbles. These air bubbles may result in floatation of the tablet, which may increase the gastric residence time of the tablet and result in a prolonged release of the drug in the acidic environment. In addition, this enhances the total mean gastrointestinal residence time and allows for increased biavailability. This is shown schematically in FIG. 18, where the tablet progresses over time from an intact and unswollen state to a floatable matrix which is loose and clear.

The differential rate of matrix hardening is the driving principle in the novel system of the present invention, which is dependent on and controlled by the rate of liquid ingress to the tablet core. With the simultaneous time-dependent decrease in gel layer integrity, the rate of drug diffusion decreases. This phenomenon compensates for the increase in diffusion path length and decrease in the surface area of the receding core which arises from the swelling property of the polymer. Hence, better controlled, preferably zero order, drug release is achieved. The drug release process can be tailored for up to 24 hours. Control of the changes in core hardness and synchronization of the rubbery/swelling front and described receding phase boundaries as well as erosion of the dissolution front boundary (i.e. erosion of the tablet periphery) results in controlled drug release, preferably including zero order kinetics. Optionally, polymer matrix hardenings is also easily achievable through double salt interaction. This binary salt combination is also uniformly dispersed in the polymeric matrix, which through ionic interaction/complexation/molecular and/or self association, increases the relative strength and rigidity of the matrix, resulting in controlled drug release with a similar mechanism to that described above.

Drugs such as the calcium-channel blockers Diltiazem and Verapamil and the beta-adrenergic blocker Propranolol (as the hydrochloride salts), with water solubilities of 50, 8 and 5% respectively, have been used in the present invention.

One hydrophilic matrix material useful in the present invention is HPMC K4M. This is a nonionic swellable hydrophillic polymer manufactured by "The Dow Chemical Company" under the tradename "Methocel". HPMC K4M is also abbreviated as HPMC K4MP, in which the "P" refers to premium cellulose ether designed for controlled release formulations. The "4" in the abbreviation suggests that the polymer has a nominal viscosity (2% in water) of 4000. The percent of methoxyl and hydroxypropryl groups are 19–24 and 7–12, respectively. In its physical form, HPMC K4M is a free-flowing, off-white powder with a particle size limitation of 90%<100 mesh screen. There are other types of HPMC such as K100LVP, K15MP, K100MP, E4MP and E10MP CR with nominal viscosities of 100, 1500, 100000, 4000, and 10000 respectively.

Figure 16:
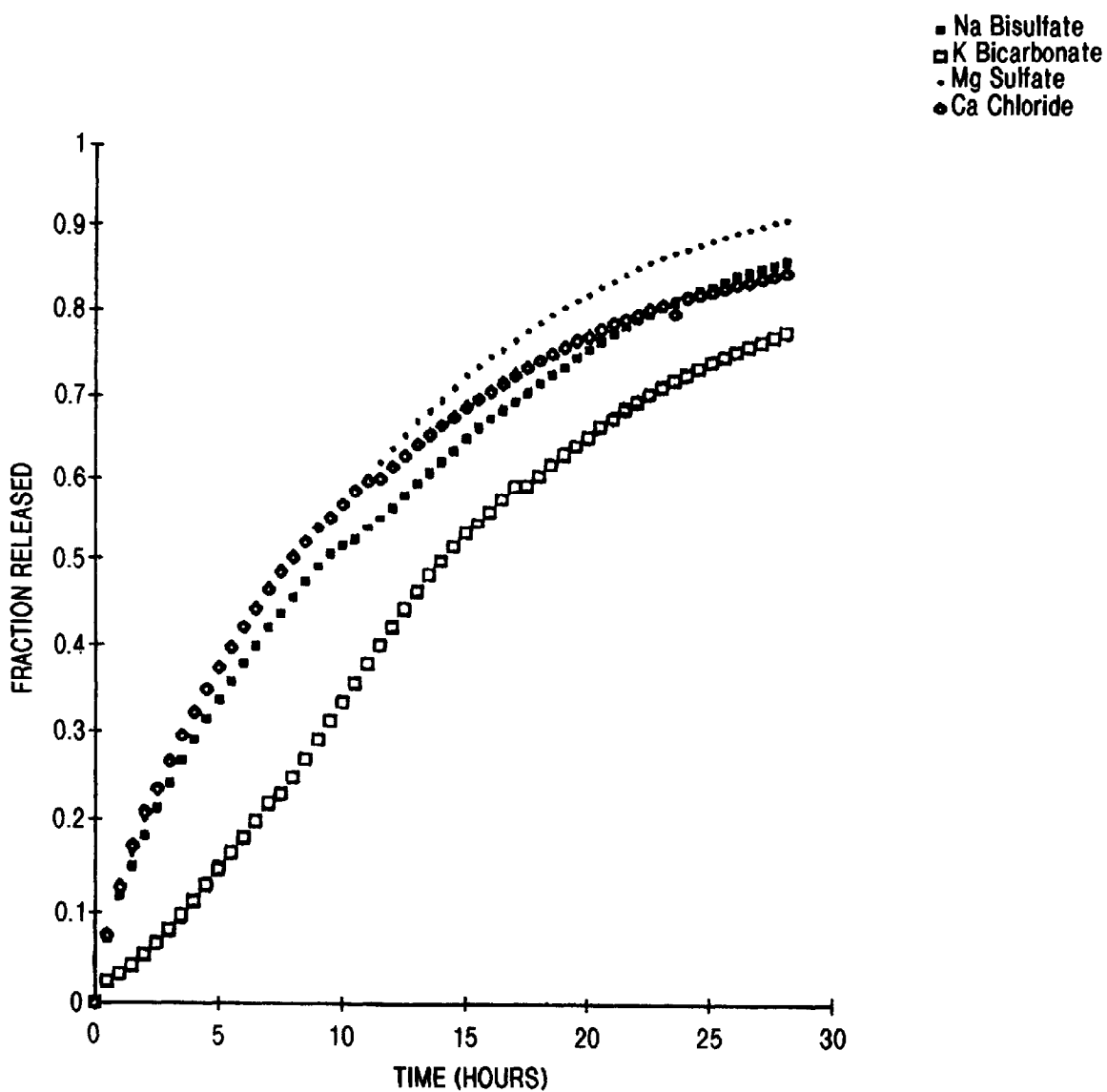
FIG. 16 is a graph showing the fractional release of diltiazem hydrochloride from tablets using salt combinations of sodium bisulfate, potassium bicarbonate, magnesium sulfate, and calcium chloride.

Formulations of the present invention may also include salts such as sodium bisulfate, potassium bicarbonate, magnesium sulfate, calcium chloride, sodium chloride, sodium sulfite and sodium carbonate in their formulations. FIG. 16 illustrates the use of some of these salts with diltiazem hydrochloride.

It is believed that an interaction between drug and salt forms a complex in the surrounding swellable matrix in a layered fashion because it occurs in a time-dependent manner as the solvent media for drug release penetrates the tablet inwardly. Likewise, because the catalyst for the initiation of drug release is liquid ingress, so too is the rate of drug release controlled by the inwardly progressive hardening of the salt complex.

A binary salt system (e.g. calcium chloride and sodium carbonate) may also be used, may also be used, in which case the hardening reaction may be a function of interaction between the salts. Calcium chloride may be incorporated to form a complex with sodium carbonate. With this combination, the reaction products are insoluble calcium carbonate and soluble channel former, sodium chloride. Hence the calcium carbonate embeds itself in the polymer matrix, initiates hardening and slowly dissolves with liquid ingress and the subsequent creation of diffusion channels as drug diffuses out. In a similar way, other binary salt combinations display time-dependent "hardening/de-hardening" behavior.

The amount of salt to be used may easily be determined, by those skilled in the art, taking into consideration the solubility of the drug, the nature of the polymer and the required degree of matrix hardening desired. In case of diltiazem hydrochloride in a HPMC matrix, 100 mg of sodium bicarbonate provides suitable matrix hardening for zero order controlled release, while in the case of the same amount of drug in a different polymer such as polyethylene oxide, 50 mg of sodium bicarbonate appears to be ideal for the attainment of controlled zero order release.

Figure 14:
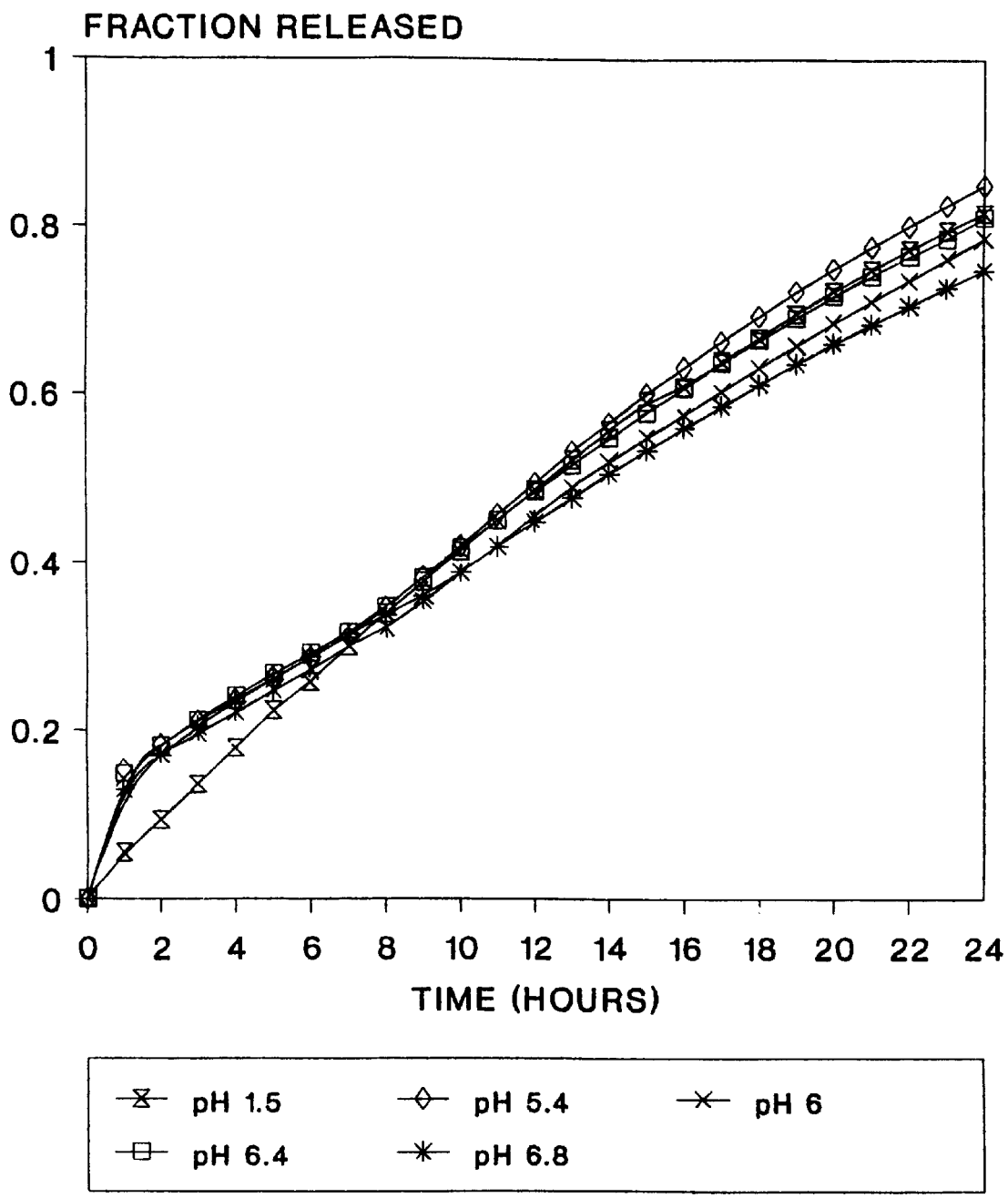
FIG. 14 is a graph showing the fractional release of diltiazem hydrochloride from tablets in accordance with Example 14 of the present invention and formulation N1 of Table 14.

On the basis of the drug release profiles presented in FIG. 14, the change in pH of the dissolution media, from acidic to basic, does not markedly change the pattern except for a burst effect at pH≧5.4, which is not a limiting factor considering the fact that the tablet will not be immediately exposed to pH 5.4 in the gastrointestinal tract, and instead must first pass through the acidic gastric environment. This has been confirmed by subjecting the formulation (A5) to a carefully synchronized test of continuous changing pH environment simulating the gastrointestinal tract. This has been achieved with the aid of the Bio Dis Release Rate Tester (Vankel Instruments). The resulting drug release profile is provided in FIG. 17. The addition of salt in the formulation is not used as a pH modifying agent. Therefore, the relative salt proportion is essentially irrelevant with respect to changes in pH.

EXAMPLES

The formulations of the inventions are illustrated by the following examples. The use of particular polymers, buffers, and inert additive and fillers in the particular amounts shown are not intended to limit the scope of this invention but are exemplary only. All ingredients are initially individually massed and simultaneously incorporated. The premix is blended in a V-blender. The resultant homogeneous powder is compressed into tablets using conventional technologies.

Example 1

| FORMULATIONS INGREDIENTS | FORMULATIONS (mg/tablet) | | | | |
|---|---|---|---|---|---|
| | A1 (ctrl) | A2 | A3 | A4 | A5 |
| Diltiazem HCl | 100 | 100 | 100 | 100 | 100 |
| HPMC K4M | 200 | 200 | 200 | 200 | 200 |
| Sodium bicarbonate | 0 | 10 | 50 | 75 | 100 |
| TOTAL WEIGHT OF TABLET | 300 | 310 | 350 | 375 | 400 |
| DISSOLUTION CONDITIONS | | | | | |
| Medium: | Potassium chloride buffer pH 1.5 | | | | |
| Volume: | 900 ml | | | | |
| Apparatus: | Rotating paddle | | | | |
| RPM: | 50 | | | | |

Figure 1:
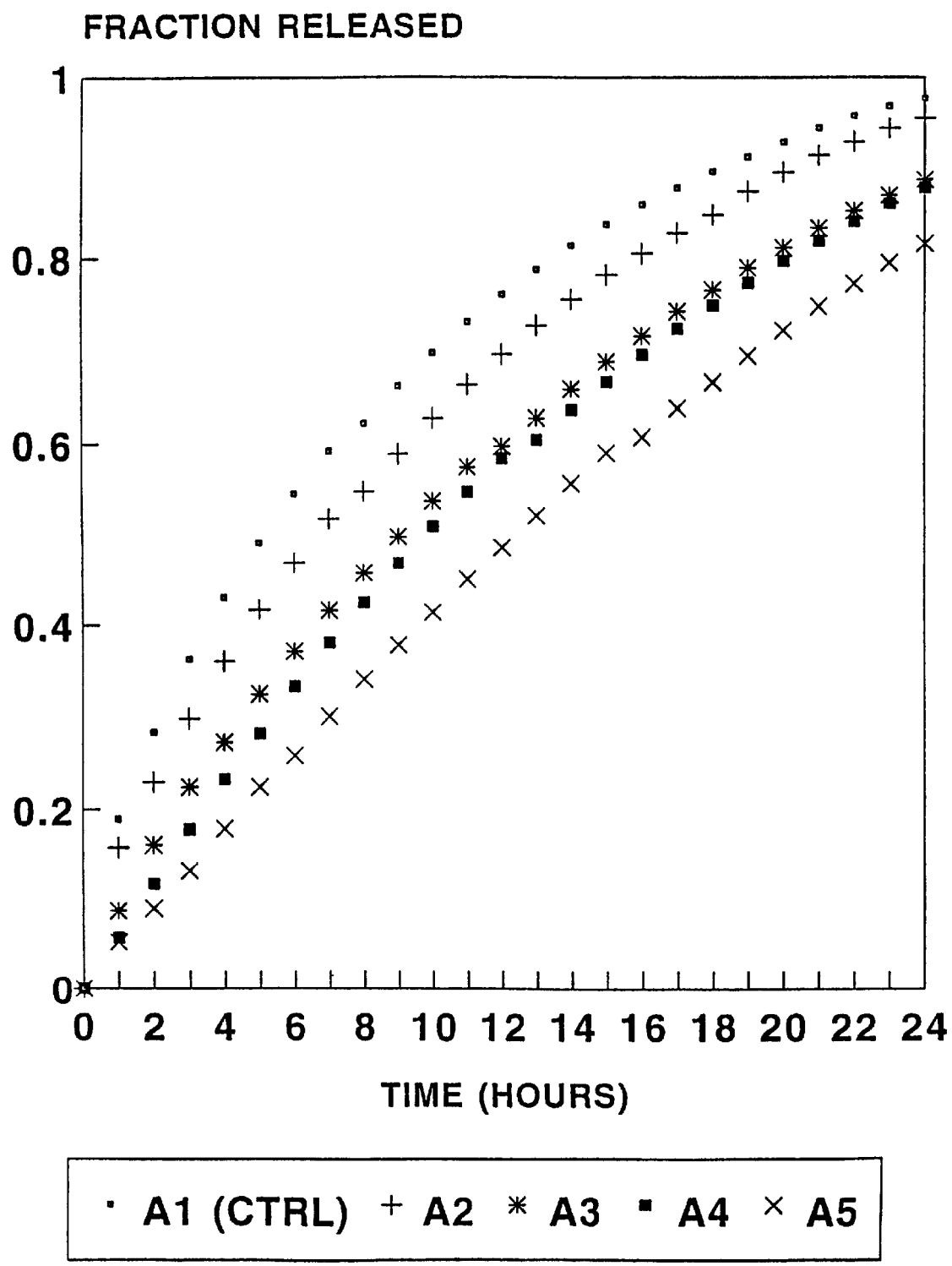
FIG. 1 is a graph showing the fractional release of diltiazem hydrochloride from tablets in accordance with Example 1 of the present invention and formulations A1–A5 of Table 1.

As shown in FIG. 1 the results of this Example reflect a progressive decrease in the release of diltiazem hydrochloride with an increase in the sodium bicarbonate content within the HPMC matrix. This increase in salt content is accompanied by an increase in the linearity of the drug release profiles. In particular, formulation A5, which contains 100 mg of sodium bicarbonate provides drug release which most closely approaches zero order over a 24-hour period.

Example 2

| FORMULATIONS INGREDIENTS | FORMULATIONS (mg/tablet) | | | | |
|---|---|---|---|---|---|
| | B1 (ctrl) | B2 | B3 | B4 | B5 |
| Diltiazem HCl | 100 | 100 | 100 | 100 | 100 |
| PEO 4M | 200 | 200 | 200 | 200 | 200 |
| Sodium bicarbonate | 0 | 10 | 50 | 75 | 100 |
| TOTAL WEIGHT OF TABLET | 300 | 310 | 350 | 375 | 400 |
| DISSOLUTION CONDITIONS | | | | | |
| Medium: | Potassium chloride buffer pH 1.5 | | | | |
| Volume: | 900 ml | | | | |
| Apparatus: | Rotating paddle | | | | |
| RPM: | 50 | | | | |

Figure 2:
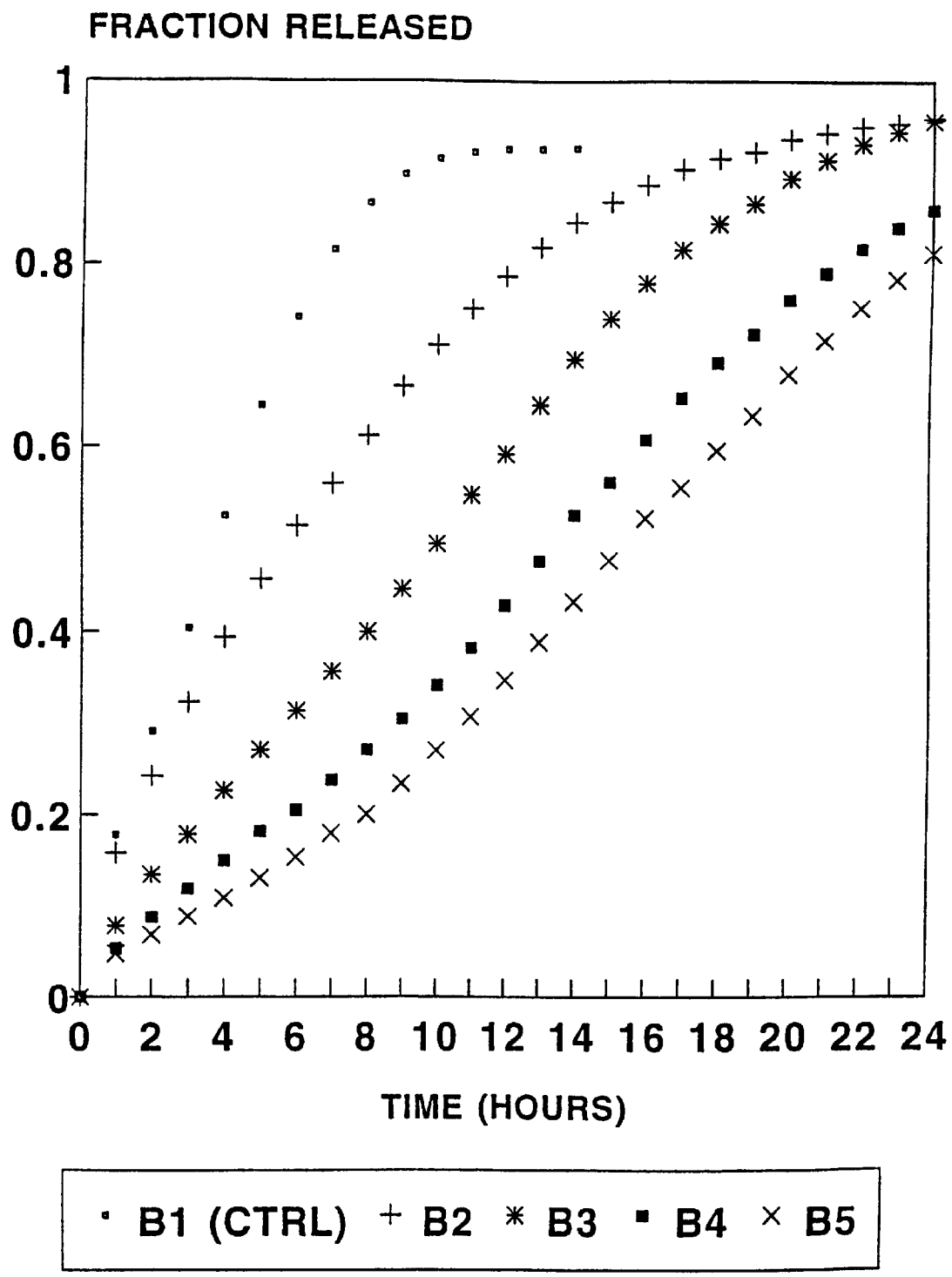
FIG. 2 is a graph showing the fractional release of diltiazem hydrochloride from tablets in accordance with Example 2 of the present invention and formulations B1–B5 of Table 2.

This Example demonstrates, as depicted in FIG. 2, that salt induced controlled drug release is also observed with polyethylene oxide as the polymeric matrix. This suggests that the present invention is not polymer-limited. The linearity in profiles seen at even the lowest salt concentration, 10 mg. At higher concentrations (above 50 mg), the profiles tend to become concave, which suggests that the level of salt required for linear drug release is lower for polyethylene oxide than for HPMC.

Example 3

| FORMULATIONS INGREDIENTS | FORMULATIONS (mg/tablet) | | | | |
|---|---|---|---|---|---|
| | C1 (ctrl) | C2 | C3 | C4 | C5 |
| Diltiazem HCl | 100 | 100 | 100 | 100 | 100 |
| HPMC K4M | 200 | 200 | 200 | 200 | 200 |
| Sodium carbonate | 0 | 10 | 50 | 75 | 100 |
| TOTAL WEIGHT OF TABLET | 300 | 310 | 350 | 375 | 400 |
| DISSOLUTION CONDITIONS | | | | | |
| Medium: | Potassium chloride buffer pH 1.5 | | | | |
| Volume: | 900 ml | | | | |
| Apparatus: | Rotating paddle | | | | |
| RPM: | 50 | | | | |

Figure 3:
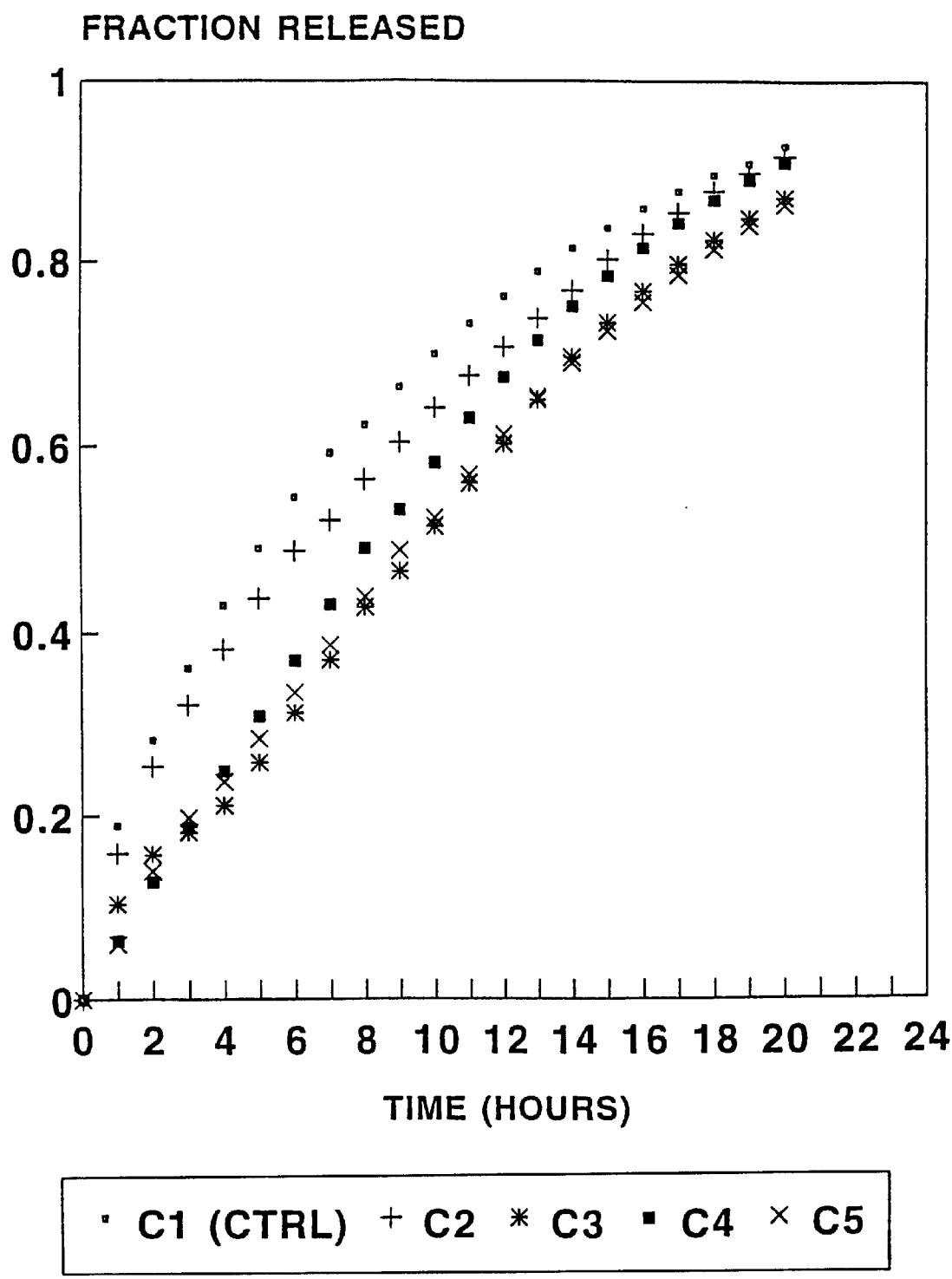
FIG. 3 is a graph showing the fractional release of diltiazem hydrochloride from tablets in accordance with Example 3 of the present invention and formulations C1–C5 of Table 3.

Example 3 demonstrates and FIG. 3 illustrates that the suppression of diltiazem release from HPMC matrices can also be attained by the application of other salts such as sodium carbonate, and linearity of release rate is still observed.

Example 4

| FORMULATIONS | FORMULATIONS (mg/tablet) | | | | |
|---|---|---|---|---|---|
| INGREDIENTS | D1 (ctrl) | D2 | D3 | D4 | D5 |
| Diltiazem HCl | 100 | 100 | 100 | 100 | 100 |
| PEO 4M | 200 | 200 | 200 | 200 | 200 |
| Sodium carbonate | 0 | 10 | 50 | 75 | 100 |
| TOTAL WEIGHT OF TABLET | 300 | 310 | 350 | 375 | 400 |
| DISSOLUTION CONDITIONS | | | | | |
| Medium: | Potassium chloride buffer pH 1.5 | | | | |
| Volume: | 900 ml | | | | |
| Apparatus: | Rotating paddle | | | | |
| RPM: | 50 | | | | |

Figure 4:
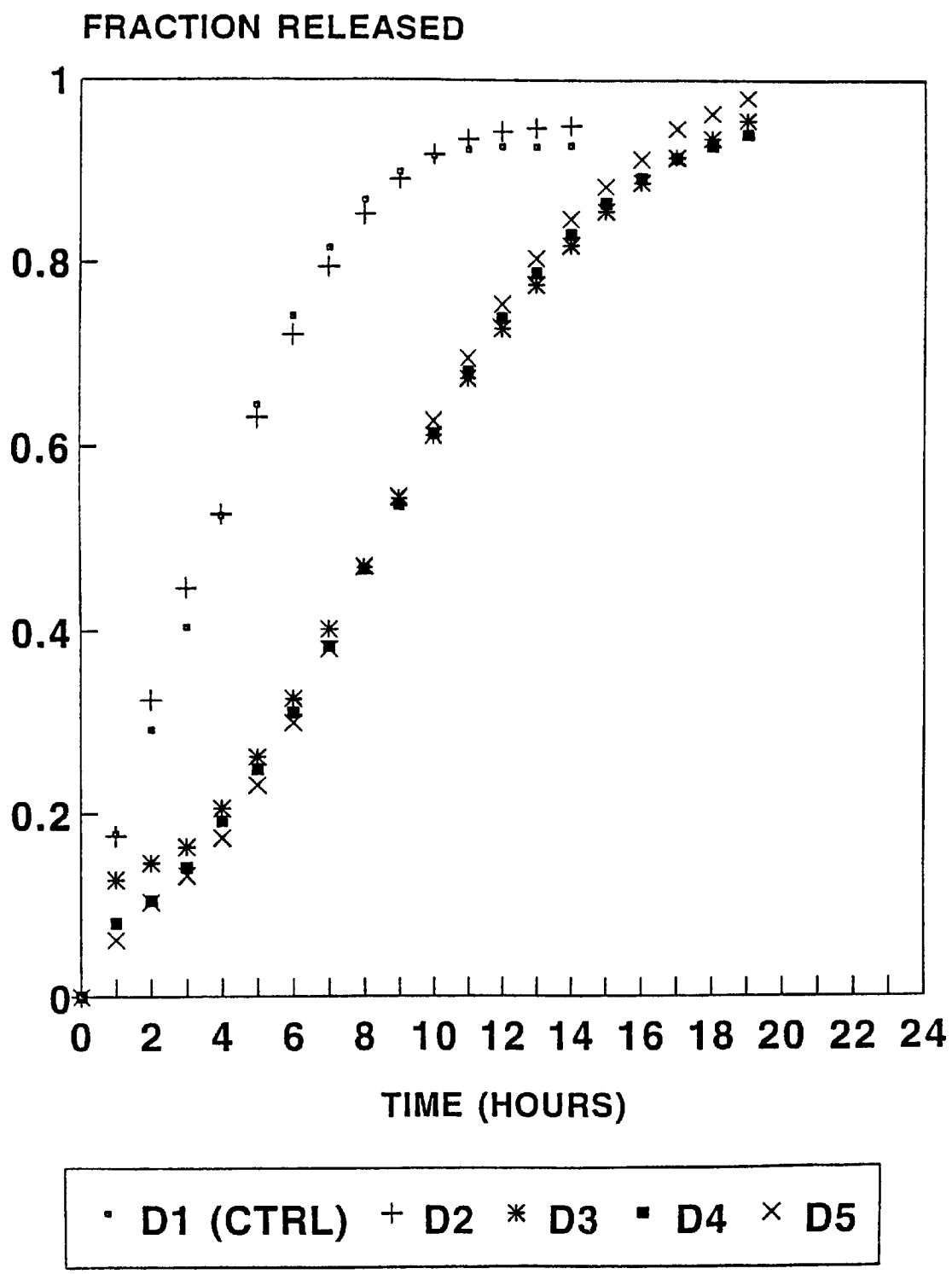
FIG. 4 is a graph showing the fractional release of diltiazem hydrochloride from tablets in accordance with Example 4 of the present invention and formulations D1–D5 of Table 4.

Example 4 demonstrates and FIG. 4 demonstrates that in using polyethylene oxide as the polymeric matrix, and sodium bicarbonate as the incorporated salt, an initial slow release followed by a more rapid linear release can be obtained. The initial slow release phase causes dilution of the drug in the gastric environment and subsequent reduction in gastrointestinal irritation.

Example 5

| FORMULATIONS | FORMULATIONS (mg/tablet) | | | | |
|---|---|---|---|---|---|
| INGREDIENTS | E1 (ctrl) | E2 | E3 | E4 | E5 |
| Diltiazem HCl | 100 | 100 | 100 | 100 | 100 |
| HPMC K4M | 200 | 200 | 200 | 200 | 200 |
| Potassium bicarbonate | 0 | 10 | 50 | 75 | 100 |
| TOTAL WEIGHT OF TABLET | 300 | 310 | 350 | 375 | 400 |
| DISSOLUTION CONDITIONS | | | | | |
| Medium: | Potassium chloride buffer pH 1.5 | | | | |
| Volume: | 900 ml | | | | |
| Apparatus: | Rotating paddle | | | | |
| RPM: | 50 | | | | |

Figure 5:
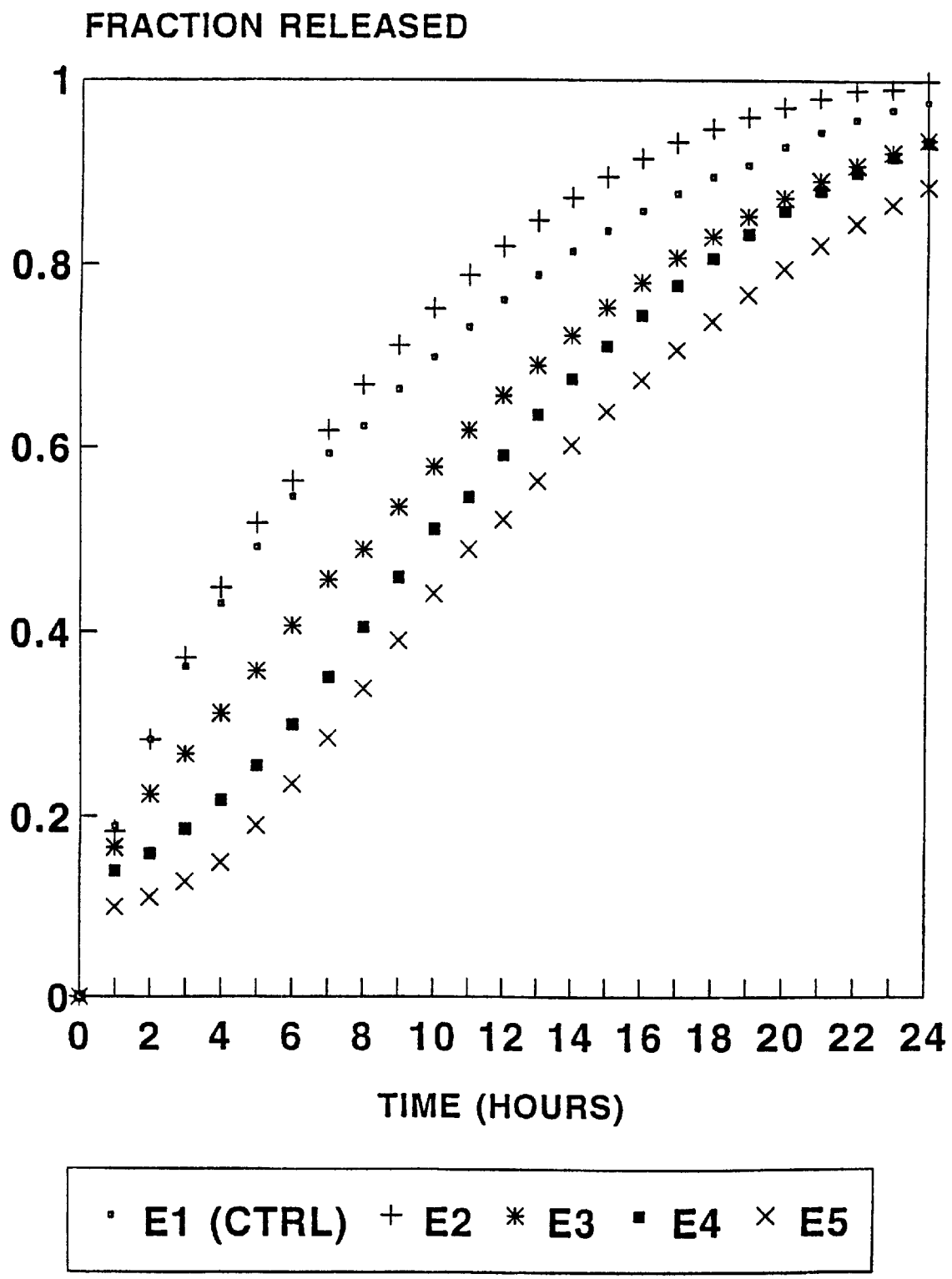
FIG. 5 is a graph showing the fractional release of diltiazem hydrochloride from the tablets in accordance with Example 5 of the present invention and formulations E1–E5 of Table 5.

As depicted in FIG. 5, Example 5 demonstrates the use of potassium bicarbonate as the incorporated salt. Linear retardation of drug release is observed after an initial burst phase corresponding to approximately 10% of the drug. This phenomenon has importance in the provision of a mini-loading dose prior to gradual metering of the drug which may be useful in some combinations.

Example 6

| FORMULATIONS | FORMULATIONS (mg/tablet) | | | | |
|---|---|---|---|---|---|
| INGREDIENTS | F1 (ctrl) | F2 | F3 | F4 | F5 |
| Diltiazem HCl | 100 | 100 | 100 | 100 | 100 |
| PEO 4M | 200 | 200 | 200 | 200 | 200 |
| Potassium bicarbonate | 0 | 10 | 50 | 75 | 100 |
| TOTAL WEIGHT OF TABLET | 300 | 310 | 350 | 375 | 400 |
| DISSOLUTION CONDITIONS | | | | | |
| Medium: | Potassium chloride buffer pH 1.5 | | | | |
| Volume: | 900 ml | | | | |
| Apparatus: | Rotating paddle | | | | |
| RPM: | 50 | | | | |

Figure 6:
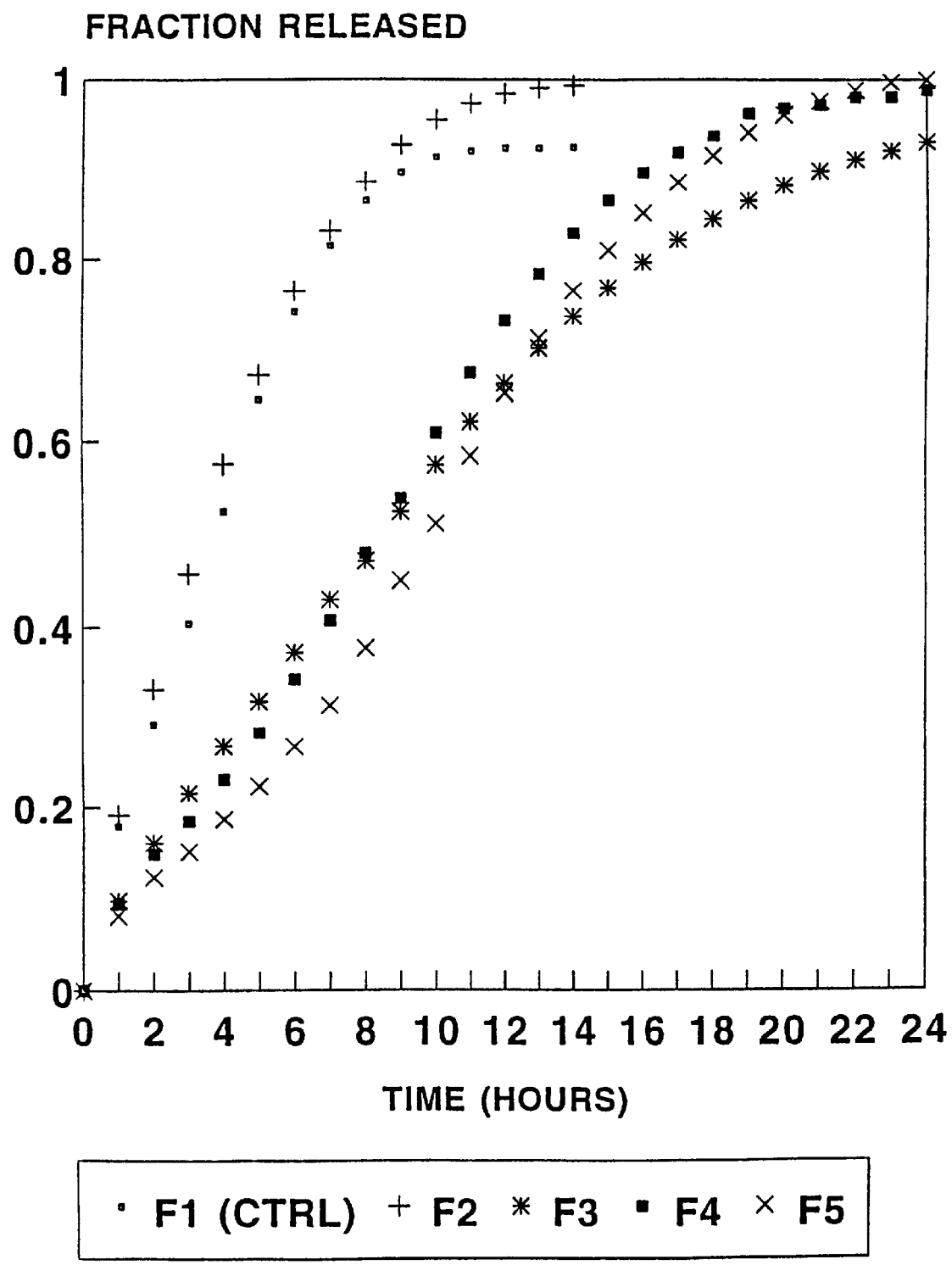
FIG. 6 is a graph showing the fractional release of diltiazem hydrochloride from tablets in accordance with Example 6 of the present invention and formulations F1–F5 of Table 6.

In this example, potassium bicarbonate is incorporated in a polyethylene matrix system. The result are seen graphically in FIG. 6. Suppression of drug release achieved while still maintaining a linear drug release. In addition, the suppression of drug release is virtually unchanged at salt concentrations beyond 50 mg/tablet.

Example 7

| FORMULATIONS | FORMULATIONS (mg/tablet) | |
|---|---|---|
| INGREDIENTS | G1 (ctrl) | G2 |
| Propanolol HCl | 100 | 100 |
| HPMC K4M | 200 | 200 |
| Sodium bicarbonate | 0 | 100 |
| TOTAL WEIGHT OF TABLET | 300 | 400 |
| DISSOLUTION CONDITIONS | | |
| Medium: | Potassium chloride buffer pH 1.5 | |
| Volume: | 900 ml | |
| Apparatus: | Rotating paddle | |
| RPM: | 50 | |

Figure 7:
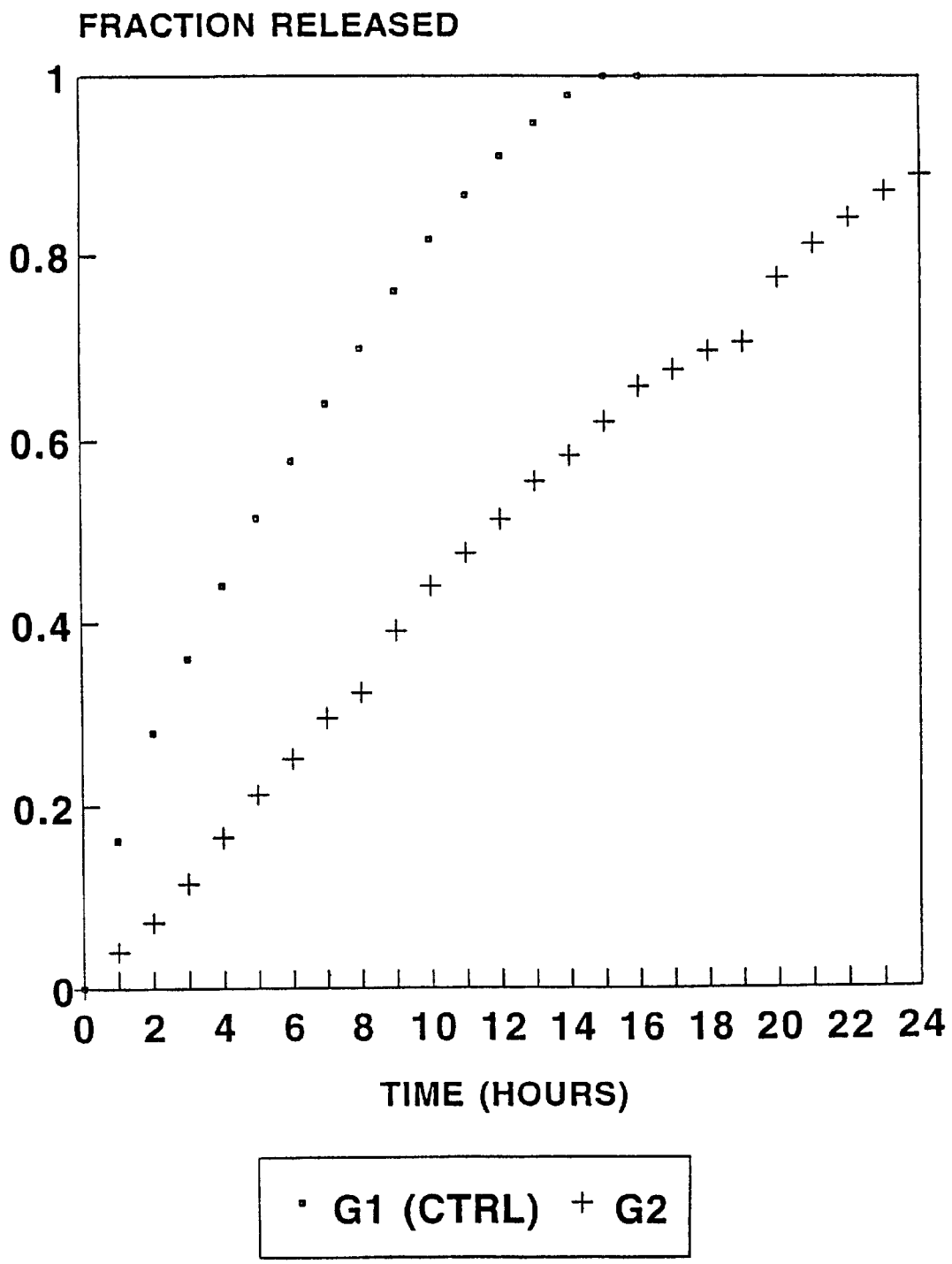
FIG. 7 is a graph showing the fractional release of Propranolol HCl from tablets in accordance with Example 7 of the present invention and formulations G1–G2 of Table 7.

This example, as depicted in FIG. 7, demonstrates that HPMC and sodium bicarbonate are a suitable combination for the release of drugs such as propranolol. The presence of sodium bicarbonate results in a substantial suppression of drug release, as compared to the use of HPMC alone.

Example 8

| FORMULATIONS | FORMULATIONS (mg/tablet) | |
|---|---|---|
| INGREDIENTS | H1 (ctrl) | H2 |
| Propanolol HCl | 100 | 100 |
| PEO K4M | 200 | 200 |
| Sodium bicarbonate | 0 | 100 |
| TOTAL WEIGHT OF TABLET | 300 | 400 |
| DISSOLUTION CONDITIONS | | |
| Medium: | Potassium chloride buffer pH 1.5 | |
| Volume: | 900 ml | |
| Apparatus: | Rotating paddle | |
| RPM: | 50 | |

Figure 8:
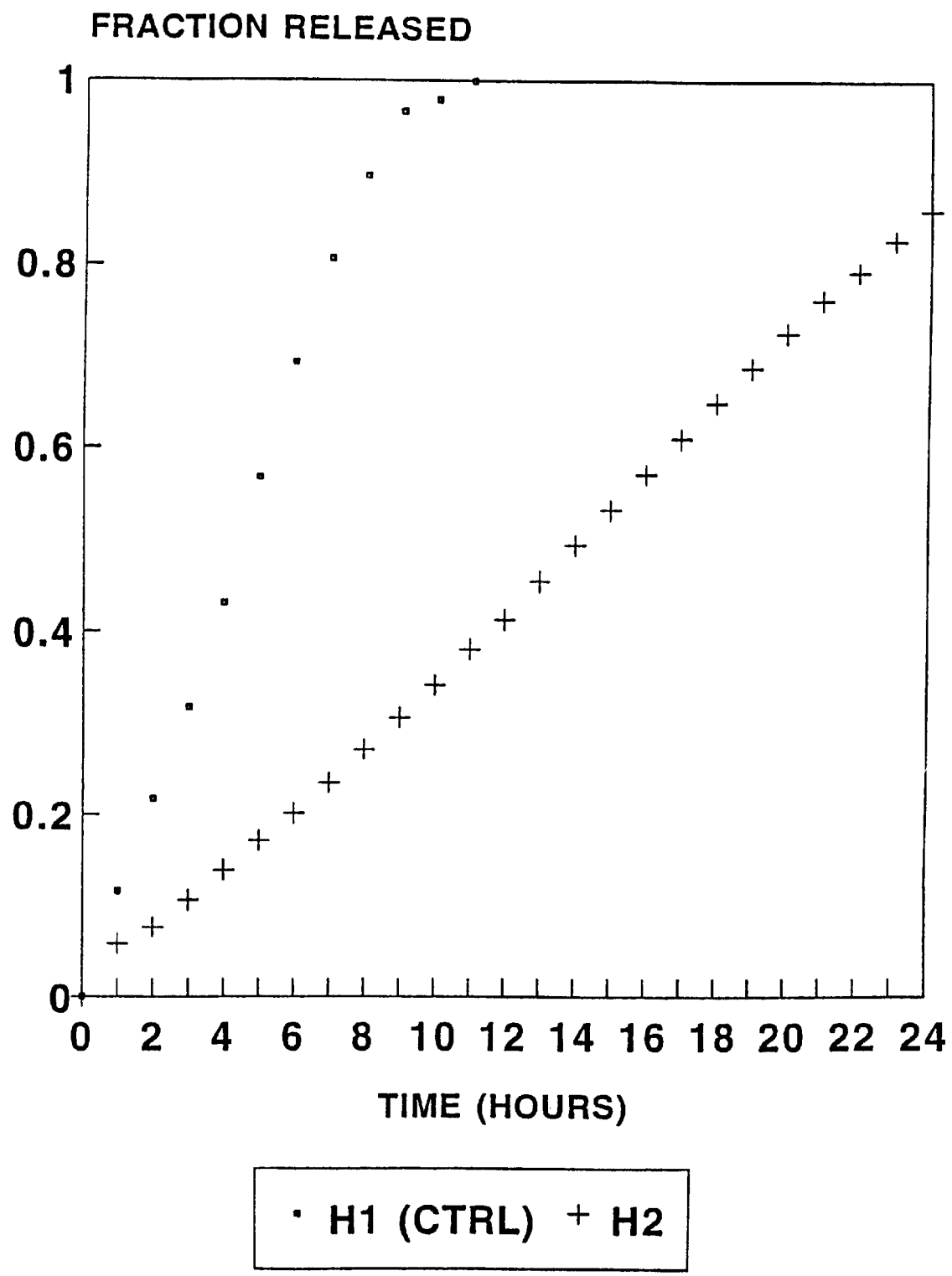
FIG. 8 is a graph showing the fractional release of Propranolol from tablets in accordance with Example 8 of the present invention and formulations H1–H2 of Table 8.

As depicted in FIG. 8, Example 8 demonstrates the use of potassium bicarbonate as the incorporated salt with polyethylene oxide as the polymeric matrix. Linear retardation of drug release is observed upon the addition of 100 mg of salt.

Example 9

| FORMULATIONS INGREDIENTS | FORMULATIONS (mg/tablet) | |
|---|---|---|
| | I1 (ctrl) | I2 |
| Verapamil HCl | 100 | 100 |
| HPMC | 200 | 200 |
| Sodium bicarbonate | 0 | 100 |
| TOTAL WEIGHT OF TABLET | 300 | 400 |
| DISSOLUTION CONDITIONS | | |
| Medium: | Potassium chloride buffer pH 1.5 | |
| Volume: | 900 ml | |
| Apparatus: | Rotating paddle | |
| RPM: | 50 | |

Figure 9:
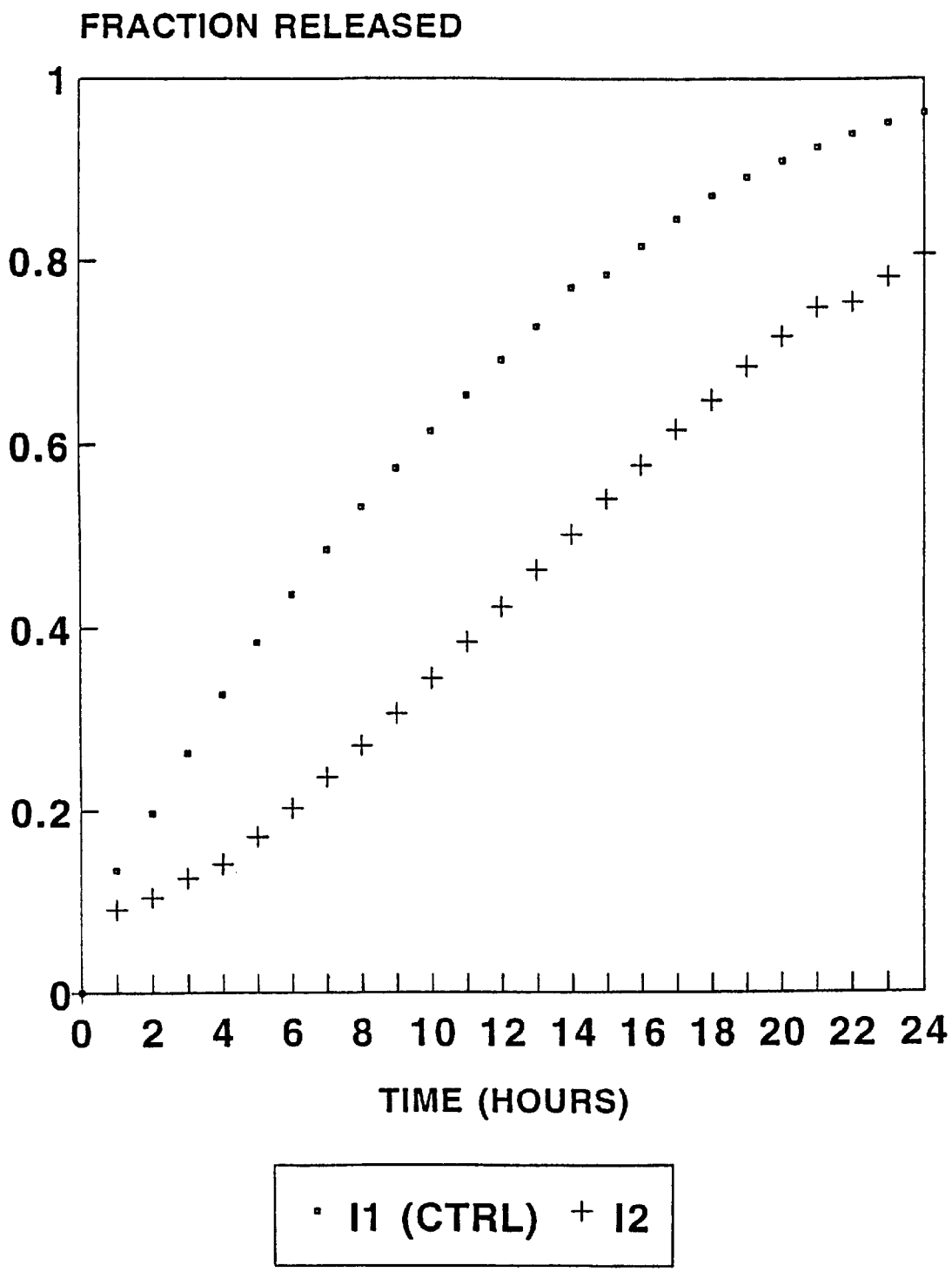
FIG. 9 is a graph showing the fractional release of Verapamil HCl from tablets in accordance with Example 9 of the present invention and formulations I1–I2 of Table 9.

The use of Verapamil HCl in the present invention is demonstrated in Example 9 and depicted in FIG. 9. As shown, the use of 100 mg of sodium bicarbonate results in a decreased rate of release of Verapamil HCl from a matrix. The formulations I1–I2 of Table 9 are particularly relevant in this regard.

Example 10

| FORMULATIONS INGREDIENTS | FORMULATIONS (mg/tablet) | |
|---|---|---|
| | J1 (ctrl) | J2 |
| Verapamil HCl | 100 | 100 |
| PEO 4M: | 200 | 200 |
| Sodium bicarbonate | 0 | 100 |
| TOTAL WEIGHT OF TABLET | 300 | 400 |
| DISSOLUTION CONDITIONS | | |
| Medium: | Potassium chloride buffer pH 1.5 | |
| Volume: | 900 ml | |
| Apparatus: | Rotating paddle | |
| RPM: | 50 | |

Figure 10:
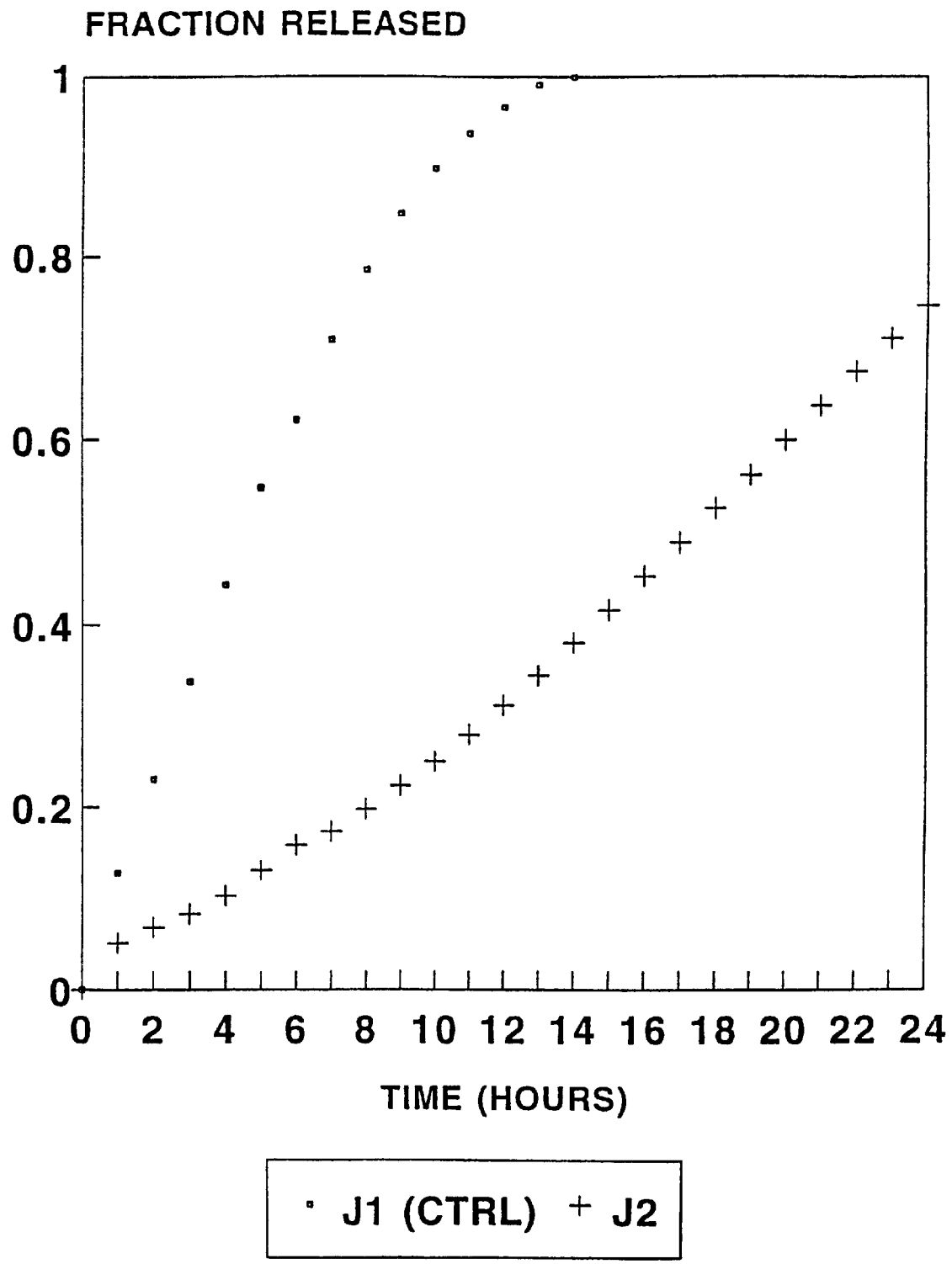
FIG. 10 is a graph showing the fractional release of Verapamil HCl from tablets in accordance with Example 10 of the present invention and formulations J1–J2 of Table 10.

Example 10 demonstrates and FIG. 10 illustrates that by selection of a suitable polymer for the matrix, a more controlled retardation of Verapamil hydrochloride may be effected. Although the release curve deviates from linearity toward concavity, such a profile is desirable when a slow onset of drug action is preferred. The concavity in release is evident only with polyethylene oxide. This is due to the sensitivity, in this combination, of the drug release profile to low salt content.

Example 11 (Comparative)

| FORMULATIONS INGREDIENTS | FORMULATIONS (mg/tablet) | |
|---|---|---|
| | K1 (ctrl) | K2 |
| Diltiazem HCl | 100 | 100 |
| HPMC K4M | 200 | 200 |
| Lactose | 0 | 150 |
| TOTAL WEIGHT OF TABLET | 300 | 450 |
| DISSOLUTION CONDITIONS | | |
| Medium: | Potassium chloride buffer pH 1.5 | |
| Volume: | 900 ml | |
| Apparatus: | Rotating paddle | |
| RPM: | 50 | |

Figure 11:
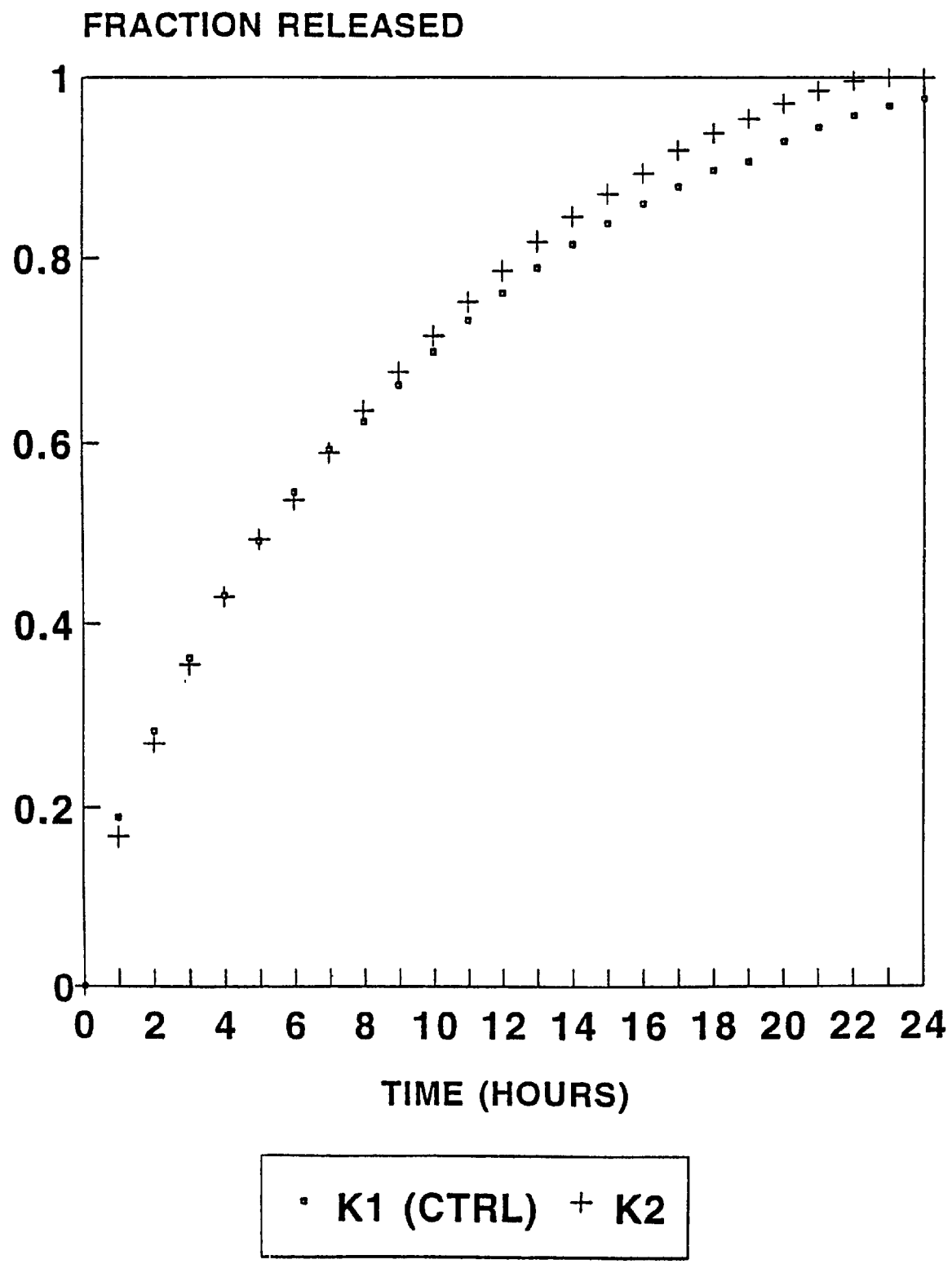
FIG. 11 is a graph showing the fractional release of diltiazem hydrochloride from tablets in accordance with Example 11 of the present invention and formulations K1–K2 of Table 11.

FIG. 11 is a graph of data from (Comparative) Example 11, showing the fractional release of diltiazem hydrochloride from hydrophillic matrix tablets in the absence of salt and with lactose as a salt substitute. The addition of 150 mg of lactose, as compared to the salt addition of other examples, resulted in no significant change in the release pattern. In this case the high solubility of diltiazem is the dominant factor in determining release rate.

Example 12

| FORMULATIONS INGREDIENTS | FORMULATIONS (mg/tablet) | |
|---|---|---|
| | L1 (ctrl) | L2 |
| Diltiazem HCl | 100 | 100 |
| HPMC K4M | 200 | 200 |
| Sodium bicarbonate | 100 | 100 |
| Lactose | 0 | 150 |
| TOTAL WEIGHT OF TABLET | 400 | 550 |
| DISSOLUTION CONDITIONS | | |
| Medium: | Potassium chloride buffer pH 1.5 | |
| Volume: | 900 ml | |
| Apparatus: | Rotating paddle | |
| RPM: | 50 | |

Figure 12:
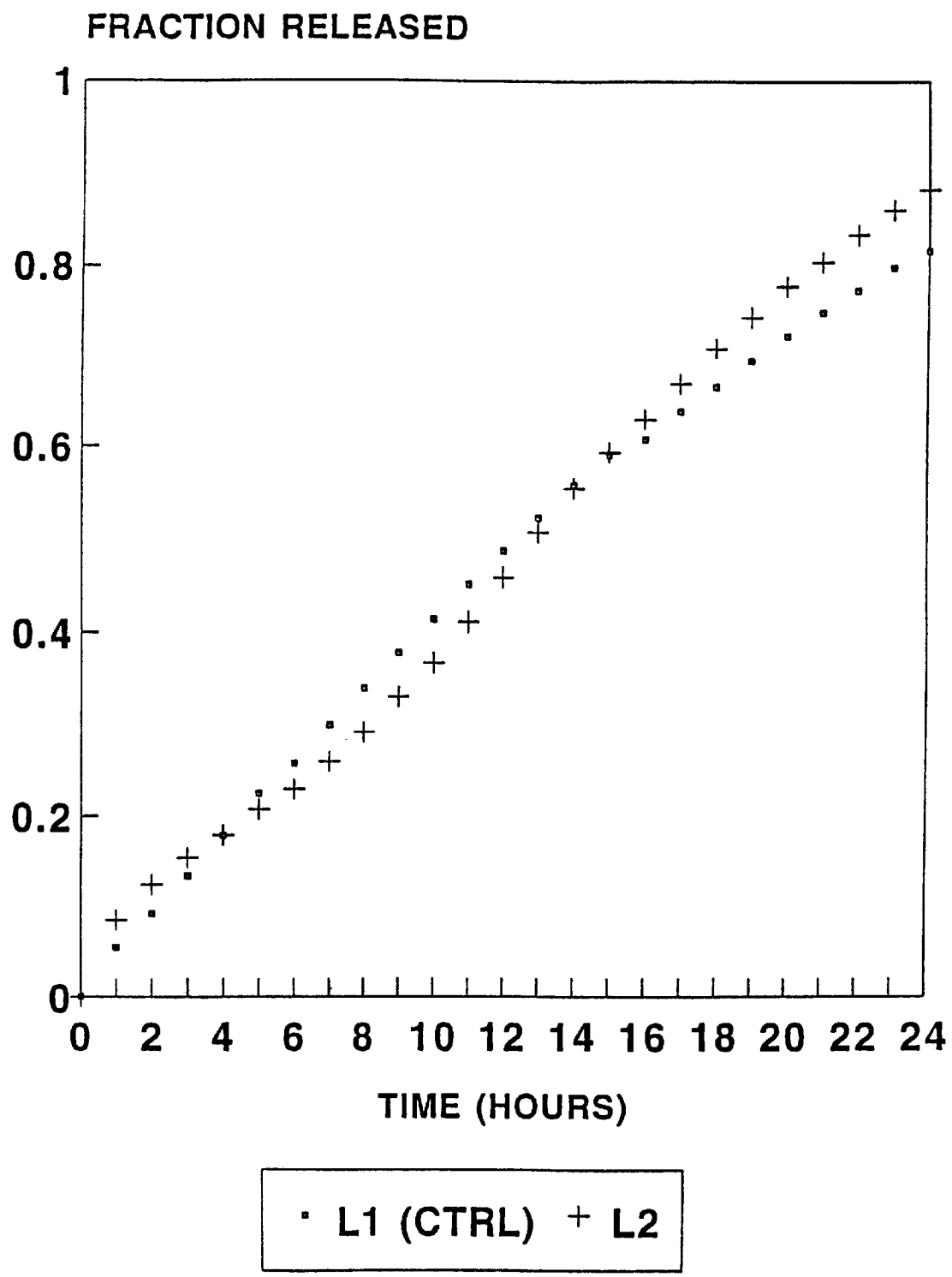
FIG. 12 is a graph showing the fractional release of diltiazem hydrochloride from tablets in accordance with example 12 of the present invention and formulations L1–L2 of Table 12.

In Example 12, as depicted in FIG. 12, compositions like those of Comparative Example 11 are modified by the addition of sodium bicarbonate. In each case, the formulations L1–L2 of Table 12 exhibit a more linear drug release rate, as compared to the control sample of Comparative Example 11. This illustrates that the presence of relatively large amounts of excipients such as lactose do not alter the principle of a drug release which is based on differential hardening rate within the matrix and in turn, results in a greater potential in formulation flexibility.

Example 13

| FORMULATIONS INGREDIENTS | FORMULATIONS (mg/tablet) | | | |
|---|---|---|---|---|
| | M1 (ctrl) | M2 | M3 | Dilacor XR ® M4* |
| Diltiazem HCl | 240 | 240 | 240 | 240 |
| HPMC K4M | 200 | 200 | 250 | n/a |
| Sodium bicarbonate | 0 | 100 | 100 | n/a |
| TOTAL WEIGHT OF TABLET | 300 | 310 | 350 | 936 |

*Commercial multitablet, multilayer preparation

DISSOLUTION CONDITIONS:

| | |
|---|---|
| Medium: | Potassium chloride buffer pH 1.5 |
| Volume: | 900 ml |
| Apparatus: | Rotating paddle |
| RPM: | 50 |

Figure 13:
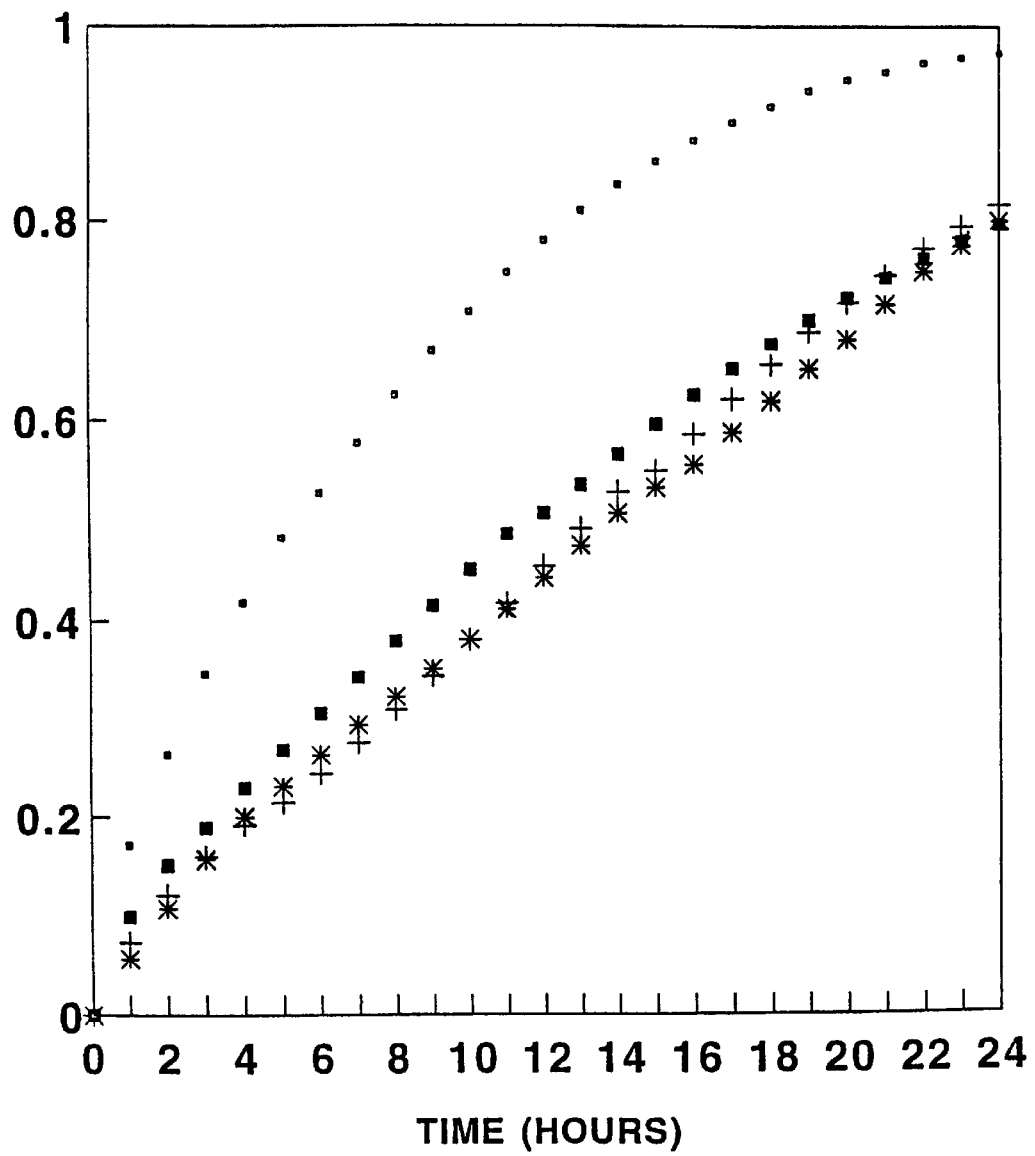
FIG. 13 is a graph showing the fractional release of diltiazem hydrochloride from tablets in accordance with Example 13 of the present invention and formulations M1–M4 of Table 13.

FIG. 13 is a graph showing the fractional release of diltiazem hydrochloride from the hydrophillic matrix tablets in accordance with Example 13 of the present invention and formulations M1–M4 of Table 13. The swellable, floatable monolithic tablet system, when formulated with a salt such as sodium bicarbonate (100 mg) exhibits a drug release profile which is similar to the commercial multilayer multitablet system of Dilacor® XR. Each commercial capsule of Dilacor® XR contains 4 three-layered tablets equivalent to 240 mg of Diltiazem hydrochloride.

Example 14

| FORMULATIONS INGREDIENTS | FORMULATIONS (mg/tablet) N1 |
|---|---|
| Diltiazem HCl | 100 |
| HPMC K4M | 200 |
| Sodium bicarbonate | 100 |
| TOTAL WEIGHT OF TABLET | 400 |

DISSOLUTION CONDITIONS

| | |
|---|---|
| Medium: | Potassium chloride buffer pH 1.5, Potassium phosphate buffers pH 5.4, 6, 6.4, and 6.8. |
| Volume: | 900 ml |
| Apparatus: | Rotating paddle |
| RPM: | 50 |

FIG. 14 demonstrates the influence of dissolution medium pH on the release of Diltiazem HCl. On exposure of the tablets to an increasingly basic environment, a more pronounced burst effect is observed, while still approaching a zero order drug release. Comparatively, a change in dissolution medium pH does not produce marked variation in drug release when compared to the release at pH 1.5.

Example 15

| FORMULATIONS INGREDIENTS | FORMULATIONS (mg/tablet) | | |
|---|---|---|---|
| | O1 (ctrl) | O2 | O3 |
| Metoprolol Tartrate | 100 | 100 | 100 |
| HPMC K4M | 200 | 200 | 200 |
| Sodium bicarbonate | — | 100 | 200 |
| Calcium chloride | — | 100 | 200 |
| TOTAL WEIGHT OF TABLET | 300 | 500 | 700 |

DISSOLUTION CONDITIONS

| | |
|---|---|
| Medium: | Deionized water pH 5.5. |
| Volume: | 900 ml |
| Apparatus: | Rotating paddle |
| RPM: | 50 |

Figure 15:
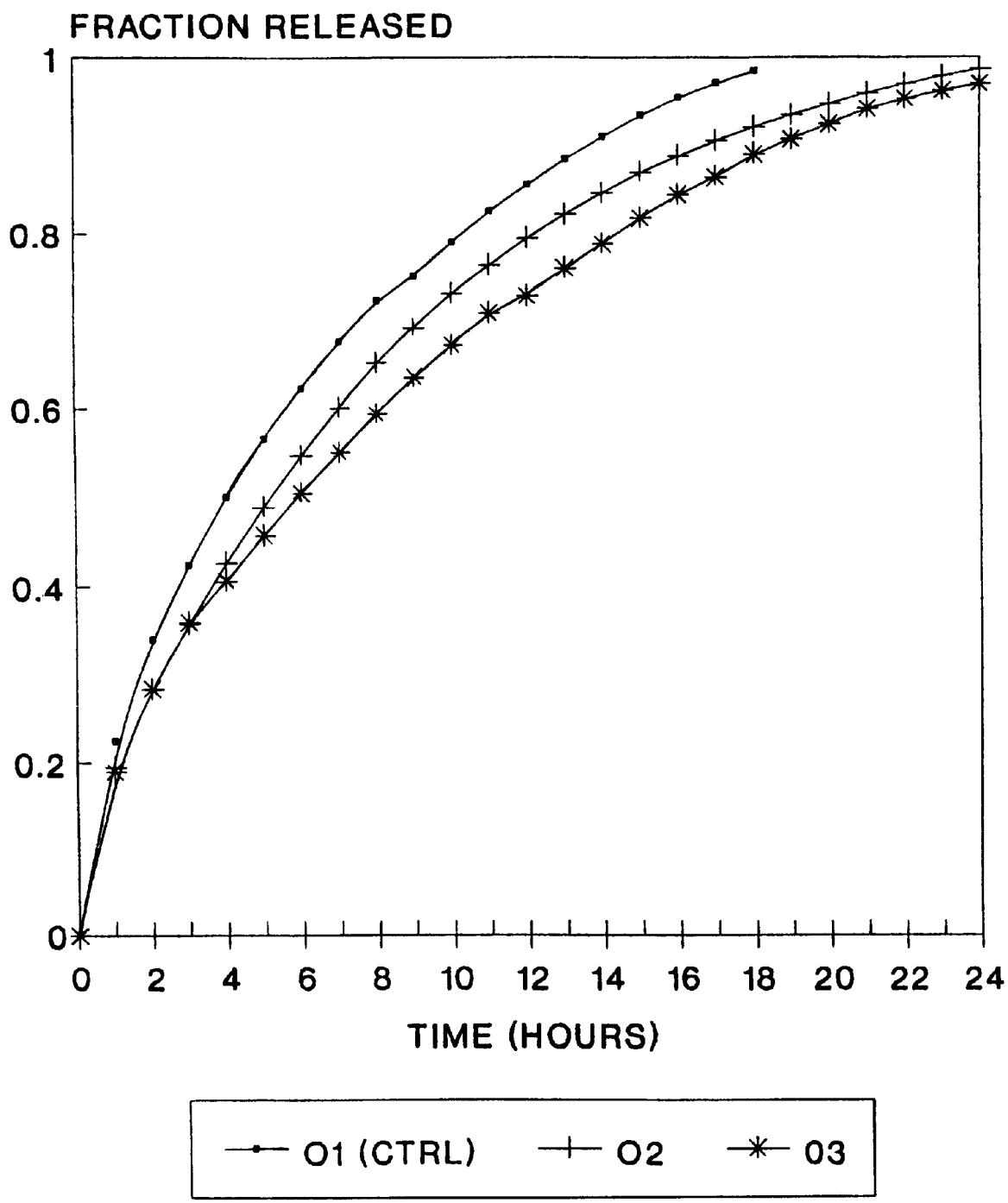
FIG. 15 is a graph showing the fractional release of Metoprolol from tablets in accordance with Example 15 of the present invention and formulations O1–O3 of Table 15.

FIG. 15 illustrates the influence of double salt interaction on the control of the 100% water soluble drug, matoprolol tartrate. As the salt content is increased from 100 to 200 mg in both cases, there is a progressive decrease in drug release. This is indicative of an increase in matrix hardening when higher salt contents are used in the formulation, which in turn causes a slower drug release effect.

Example 16

| FORMULATIONS INGREDIENTS | FORMULATIONS (mg/tablet) | | | |
|---|---|---|---|---|
| | P1 | P2 | P3 | P4 |
| Diltiazem HCl | 100 | 100 | 100 | 100 |
| HPMC K4M | 200 | 200 | 200 | 200 |
| Sodium bisulfate | 100 | 0 | 0 | 0 |
| Potassium bicarbonate | 0 | 100 | 0 | 0 |
| Magnesium chloride | 0 | 0 | 100 | 0 |
| Calcium chloride | 0 | 0 | 0 | 100 |
| TOTAL WEIGHT OF TABLET | 400 | 400 | 400 | 400 |

DISSOLUTION CONDITIONS:

| | |
|---|---|
| Medium: | Potassium chloride buffer pH 1.5 |
| Volume: | 900 ml |
| Apparatus: | Rotating paddle |
| RPM: | 50 |

Example 16, as depicted in FIG. 16, demonstrates that controlled drug release may also be attained by the use of other salts. As a result, the formulation is not be restricted to sodium bicarbonate. The quantity of salt used dictates the degree of drug release suppression which approaches zero-order.

Example 17

| FORMULATIONS | FORMULATIONS (mg/tablet) | |
|---|---|---|
| INGREDIENTS | Q1 (ctrl) | Q2 |
| Diltiazem HCl | 100 | 100 |
| HPMC K4M | 200 | 200 |
| Sodium bicarbonate | — | 100 |
| TOTAL WEIGHT OF TABLET | 300 | 400 |

DISSOLUTION CONDITIONS

Medium:  Row 1 - Potassium chloride buffer pH 1.5 (6 vessels)
Row 2 - Potassium chloride buffer pH 3 (6 vessels)
Row 3 - Potassium phosphate buffer pH 5.4 (6 vessels)
Row 4 - Potassium phosphate buffer pH 6 (6 vessels)
Row 5 - Potassium phosphate buffer pH 6.4 (6 vessels)
Row 6 - Potassium phosphate buffer pH 6.8 (6 vessels)
Duration spent by tablet in each row:
Row 1 - 4 hours
Row 2 - 0.5 hours
Row 3 - 0.5 hours
Row 4 - 6 hours
Row 5 - 6 hours
Row 6 - 7 hours
Total duration of test: 24 hours
Volume of medium in each vessel: 220 ml
Apparatus: Bio Dis Release Rate Tester (Vankel Instruments)
Dips per minute (dpm): 10

Figure 17:
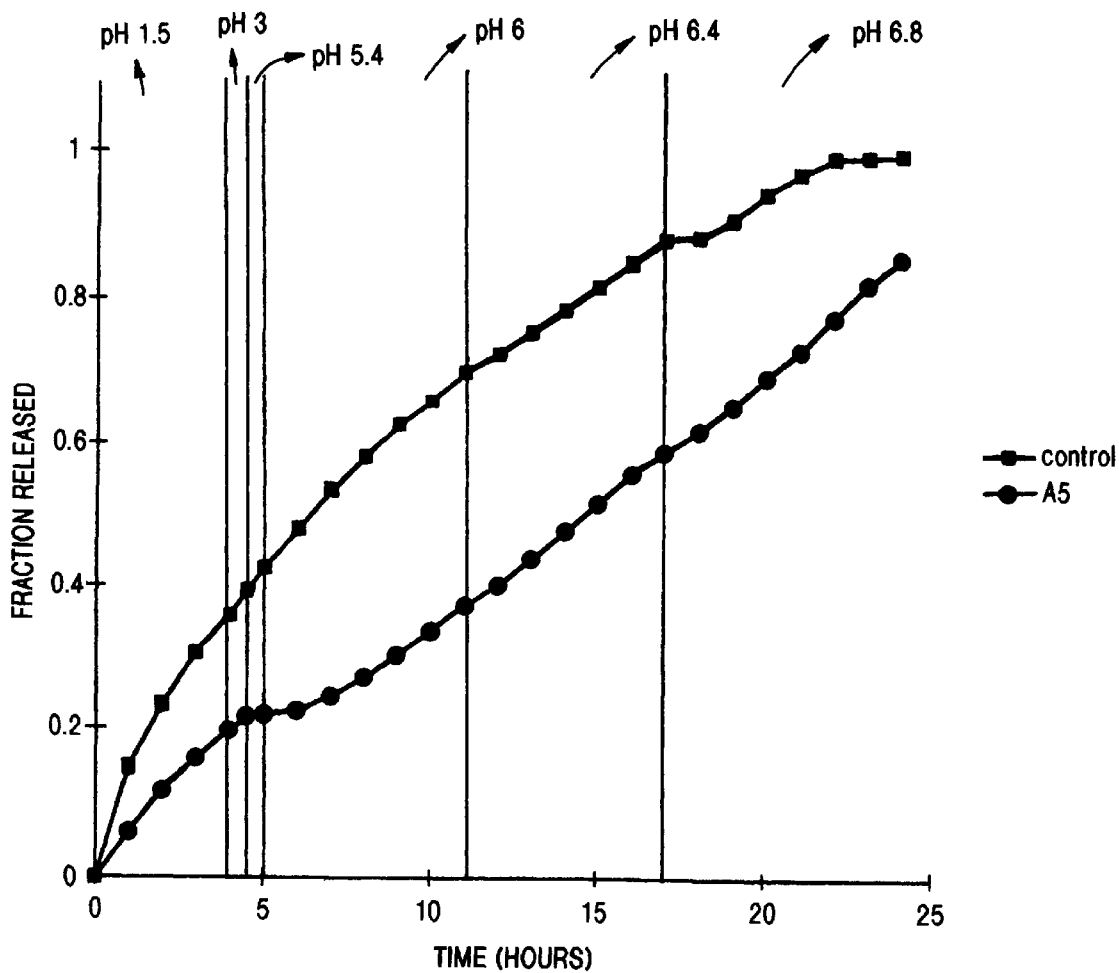
FIG. 17 is a graph showing the fractional release of formulation A5 of the present invention during exposure to continuously changing pH levels.

Example 17, as depicted in FIG. 17, illustrates that by conducting one continuous test using media which simulates the gastrointestinal milieu as well as simulating the gastrointestinal transit time, the drug release from formulation Q2 maintains essentially a controlled zero-order release. This indicates that the formulation is relatively insensitive to changes in gastrointestinal pH.

What is claimed:

1. A monolithic controlled release drug delivery tablet for improving linearity of drug delivery over a sustained period of time comprising a hydrophilic swellable polymeric matrix;
   a pharmaceutically effective amount of an active agent whose degree of solubilization is substantially independent of pH over a pH in the range of pH 1.5 to pH 7.5 dispersed in said matrix, and
   an inorganic salt dispersed in said matrix at a concentration in the range of 50% to 100% by weight of the polymeric matrix, in which upon exposure to an aqueous medium, said salt causes a hardened boundary around the periphery of the matrix, said boundary sequentially progressing inwardly toward the center thereof as said aqueous medium permeates the matrix, said hardened boundary limiting the rate at which the pharmaceutically active agent in said matrix is released from the tablet,
   with the proviso that said tablet does not include polyacrylic acid or its pharmaceutically acceptable salt and said tablet is a compressed blend of homogeneous powders comprising said polymeric matrix, said active agent, and said salt.

2. A monolithic controlled release drug delivery tablet for improving linearity of drug delivery over a sustained period of time as recited in claim 1 wherein said salt is selected from the group consisting of sodium chloride, sodium bicarbonate, potassium bicarbonate, sodium citrate, sodium bisulfate, sodium sulfite, magnesium sulfate, calcium chloride, potassium chloride, and sodium carbonate.

3. A monolithic controlled release drug delivery tablet for improving linearity delivery over a sustained period of time as recited in claim 1 wherein said hydrophilic swellable polymeric matrix is hydroxypropylmethylcellulose or polyethylene oxide.

4. A monolithic controlled release drug delivery tablet for improving linearity of drug delivery over a sustained period of time as recited in claim 1 wherein said pharmaceutically active agent is of high water solubility.

5. A monolithic controlled release drug delivery tablet for improving linearity of drug delivery over a sustained period of time as recited in claim 1 wherein said pharmaceutically active agent is of low water solubility.

6. A monolithic controlled release drug delivery tablet for improving linearity of drug delivery over a sustained period of time as recited in claim 1 wherein said pharmaceutically active agent is diltiazem, propranolol, or verapamil.

7. A monolithic controlled release drug delivery tablet for improving linearity of drug delivery over a sustained period of time consisting of:
   a hydrophilic swellable polymeric matrix;
   a pharmaceutically effective amount of an active agent dispersed in said matrix, said active agent having a degree of solubilization which is substantially independent of pH over a pH in the range of pH 1.5 to pH 7.5; and
   a salt dispersed in said matrix at a concentration in the range of 50% to 100% by weight of the polymeric matrix, said salt being selected from one or two members of the group consisting of sodium chloride, sodium bicarbonate, potassium bicarbonate, sodium citrate, sodium bisulfate, sodium sulfite, magnesium sulfate, calcium chloride, potassium chloride, and sodium carbonate,
   in which upon exposure to an aqueous medium, said salt causes a hardened boundary around the periphery of the matrix, said boundary sequentially progressing inwardly toward the center thereof as said aqueous medium permeates the matrix, said hardened boundary limiting the rate at which the pharmaceutically active agent in said matrix is released from the tablet,
   with the proviso that said tablet is a compressed blend of homogeneous powders comprising said polymeric matrix, said active agent, and said salt.

* * * * *